United States Patent [19]
VanWinkle et al.

[11] Patent Number: 5,375,278
[45] Date of Patent: Dec. 27, 1994

[54] THERAPEUTIC PILLOW AND METHOD

[76] Inventors: Tresa A. VanWinkle; Larry K. VanWinkle, both of 1005 Spruce, Alamogordo, N. Mex. 88310-4919

[21] Appl. No.: 199,386
[22] Filed: Feb. 18, 1994
[51] Int. Cl.$^5$ .......................... A47C 20/00; A61F 7/00
[52] U.S. Cl. ................................... 5/644; 5/640; 5/490; 607/112; 607/114
[58] Field of Search .................. 5/448, 450, 421, 490, 5/639, 640, 644; 607/112, 114

[56] References Cited

U.S. PATENT DOCUMENTS

| | | | |
|---|---|---|---|
| 3,426,372 | 2/1969 | Enelow | 5/490 X |
| 4,163,297 | 8/1979 | Neumark | 5/446 |
| 4,381,025 | 4/1983 | Schooley | 607/112 |
| 4,777,346 | 10/1988 | Swanton | 219/313 |
| 4,805,619 | 2/1989 | Swearingen | 607/112 X |
| 4,843,662 | 7/1989 | Handleman | 5/481 |
| 4,887,326 | 12/1989 | O'Brien et al. | 5/490 X |
| 4,985,951 | 1/1991 | Lacotte et al. | 5/465 |
| 5,033,137 | 7/1991 | Pedrow | 5/436 |
| 5,138,728 | 8/1992 | Aston | 5/645 |
| 5,163,194 | 11/1992 | Dixon | 5/636 |
| 5,274,865 | 1/1994 | Takehashi | 5/421 X |
| 5,300,104 | 4/1994 | Gaudreault et al. | 607/114 |
| 5,300,105 | 4/1994 | Owens | 607/114 |

OTHER PUBLICATIONS

Advertisement, "Elasto-Gel Hot/Cold Therapy Wraps," *Prevention Magazine*, (Feb. 1994).
Advertisement, "Micro" gel neck wrap, *Taylor Gifts*, (Jan. 1994).
Advertisement, "Hot/Cold Beauty Mask," *Beauty Boutique*, (Winter 1994).
Advertisement, "Comfort Pillow," *Voice of the Mountains*, (Dec. 1993).

*Primary Examiner*—Michael F. Trettel
*Attorney, Agent, or Firm*—Armijo, Baca & Torres

[57] ABSTRACT

Disclosed is a therapeutic pillow having a removable washable outer sleeve. The pillow has a baglike cover filled with natural granular material having a water content in the range of 5% to 25% by weight. The preferred range of water content is from 9% to 16%.

Also disclosed is a method of treating pain with the therapeutic pillow.

11 Claims, 1 Drawing Sheet

A-A

THERAPEUTIC PILLOW AND METHOD

BACKGROUND OF THE INVENTION

1. Field of the Invention (Technical Field) The invention relates to a portable therapeutic pillow which can be either heated or cooled to relieve bodily pain and promote comfort.

2. Background Art

Hot and cold packs have long been used to ameliorate bodily discomfort. The well known hot water bottle and ice pack have long been in human service: for example, hot water bottles for warming the body and loosening taut muscles; ice packs for reducing swelling and soothing sprains and strains. Variations upon these devices proliferate in the prior art.

U.S. Pat. No. 4,163,297, to Neumark, entitled *Mattress,* discloses a mattress comprising a plurality of individual pillows for preventing decubitus ulcers (bed sores). The pillows may be filled with grain-like material. There is, however, no disclosure relating to heating, cooling or moisture content of the pillows.

U.S. Pat. No. 4,777,346, to Swanton, Jr., entitled *Electrically Heated Therapeutic Pillow,* discloses a liquid or gel filled pillow. Heating is accomplished by electric current, flow of which is facilitated by compression of conductive foam. U.S. Pat. No. 5,033,137, to Pedrow, entitled *Orthopedic pillow with Groove for Spine,* discloses an orthopedic pillow having a grooved structure for spinal accommodation. A bladder similar to an ice pack or hot water bottle is also provided for warming and cooling. U.S. Pat. No. 5,163,194, to Dixon, entitled *Adjustable Cervical Pillow,* discloses a polyurethane foam pillow having a removal, supplemental member which can be a heat pack or a cold pack.

U.S. Pat. No. 4,843,662, to Handelman, entitled *Two Person Seat Case,* discloses a stadium seat having straps. U.S. Pat. No. 5,138,728, to Aston, entitled *Interior Container Insert For Any Pillow, Cushion or Stuffed Toy* discloses a removable, washable container adapted to be inserted into any pillow, cushion or stuffed toy to secrete valuables therein. U.S. Pat. No. 4,985,951, to Lacotte, et al., entitled *Flexible Mattress Including Vegetable Fibers,* discloses a mattress composed, in part, of coconut fibers.

None of the prior art, however, discloses a therapeutic pillow having a natural granular or grain-like filling having a moisture content in the range of 5% to 25% by weight.

SUMMARY OF THE INVENTION (DISCLOSURE OF THE INVENTION)

In accordance with the present invention, there is provided an apparatus and method for applying heat or cold to a body part for ameliorating discomfort. The preferred apparatus of the invention is a therapeutic pillow comprising a removable outer sleeve, a baglike covering within the removable outer sleeve, the baglike covering containing a filling comprising natural granular material, and the natural granular material comprising a water content having a range of 5% to 25% by weight.

The preferred outer sleeve is washable. The preferred washable outer sleeve comprises terry cloth fabric.

The preferred baglike covering comprises cotton fabric.

The preferred baglike covering also comprises ears.

The preferred filling comprising natural granular material comprises processed barley. The filling comprising natural granular material also comprises seeds. The preferred water content of the natural granular material comprises a range of from 9% to 16% by weight.

The preferred method of treating pain in an affected body part comprises the steps of providing an eared baglike covering, filling the eared baglike covering with natural granular material having a water content within the range of 5% to 25% by weight, loosely surrounding the eared baglike covering with a removal outer sleeve, heating or cooling the filled baglike covering and removable outer sleeve and applying the heated or cooled filled baglike covering and removable outer sleeve to the affected body part.

The preferred step of filling the eared baglike covering with natural granular material comprises the step of filling the eared baglike covering with barley. The step of filling the eared baglike covering with natural granular material can also comprise of filling the eared baglike covering with seeds. The step of filling also comprises filling the eared baglike covering with natural granular material having a water content within the range of 9% to 16% by weight.

A primary object of the present invention is the provision of a portable therapeutic pillow capable of selectively heating or cooling a variety of body parts.

Another object of the invention is the provision of a therapeutic pillow which is environmentally and anatomically safe.

Still another object of the invention is the provision of a therapeutic pillow that does not require electrical cords or batteries.

Yet another object of the invention is the provision of a therapeutic pillow which is of selected weight, shape, texture and mass to readily conform to selected body parts.

A primary advantage of the present invention is its low cost and ease of manufacture.

Another advantage of the invention is its flexibility and ease of application.

Still another advantage of the invention is its construction of naturally occurring materials.

Yet another advantage of the invention is its safety when heating a body part.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating a preferred embodiment of the invention and are not to be construed as limiting the invention. In the drawings.

DESCRIPTION OF THE PREFERRED EMBODIMENTS (BEST MODES FOR CARRYING OUT THE INVENTION)

Application of heat and cold have long been recognized as therapeutic for localized ailments. Localized application of cold, for example, may relieve stress headaches, inflammation and swelling, and the pain of arthritis, minor burns and wounds, and the like. Cold promotes vasoconstriction, thereby preventing swelling while promoting coagulation. Localized application of heat, for example, may promote healing and relieve pain resulting from arthritis, minor wounds, muscle strains, menstrual cramps, and the like. Heat promotes vasodilation, thereby improving blood flow to injured bodily parts.

Figure 1:
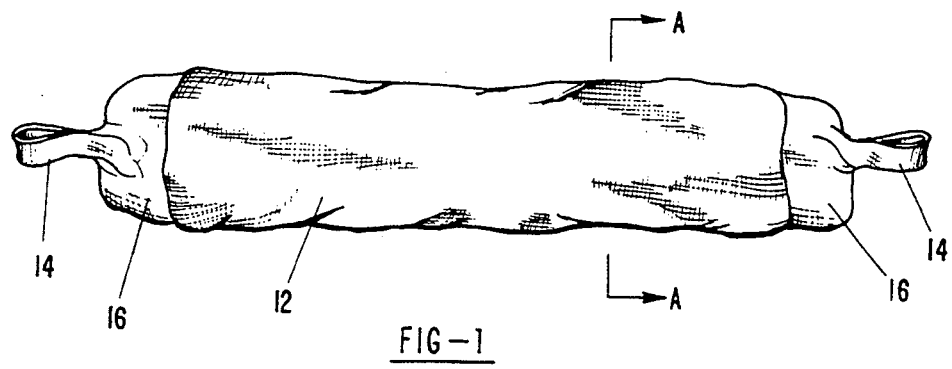
FIG. 1 is a perspective view of an elongated cylindrical embodiment of the invention.
Figure 2:
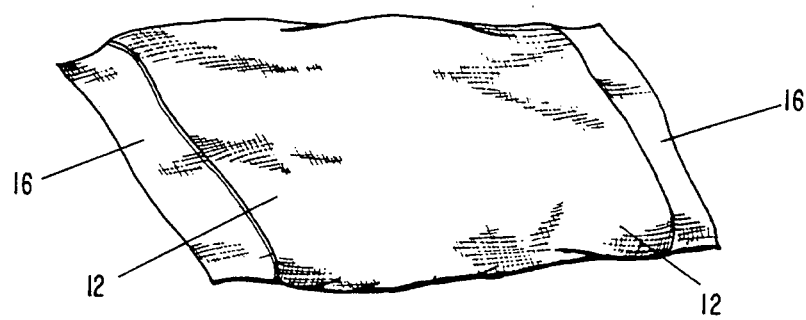
FIG. 2 is a perspective view of an oblong rectangular embodiment of the invention.
Figure 3:
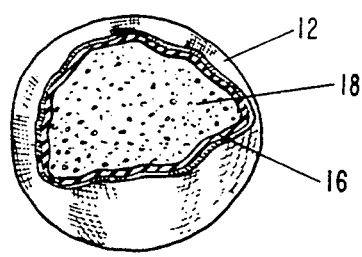
FIG. 3 is a perspective view of a spherical embodiment of the invention.
Figure 4:
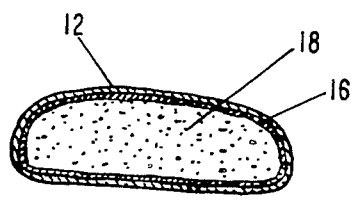
FIG. 4 is a cross-sectional view along A—A' of FIG. 1.

FIGS. 1 and 4 depict the preferred therapeutic pillow 10 of the invention. A tubular outer sleeve preferably of terry cloth, partially surrounds therapeutic pillow 10. Sleeve 12 in addition to protecting and cooling the pillow is washable. Further, sleeve 12 provides a convenient "tuck" for ears 14, as will be described later. Sleeve 12 may also comprise other natural fibers, for example, wool, cotton, and the like.

Therapeutic pillow 10 further comprises inner baglike cover 16. Inner cover 16 is also comprised of suitable natural fibers, preferably cotton, or other natural fiber materials. Alternatively inner baglike cover 16 can comprise of any material capable of efficiently transferring heat and containment of filling 18. Inner baglike cover 16 is partially filled with filling 18.

Filling 18 comprises naturally occurring grains or granular material. The preferred filling is processed barley, but other natural grains, seeds and natural granular material may be used. The use of such natural materials is important in several respects.

Use of naturally occurring granular and grain-like materials provides "live" weight and mass to the therapeutic pillow. Accordingly, therapeutic pillow 10 can be shaped to conform to any given anatomical area, be it arms, legs, neck, spine, and the like. Further, because of its weight and mass, such conformable shape will tend to be maintained while in position against the body part. Although this specification refers to a tubular form, other forms can be utilized to conform to other body members.

Additionally, and most importantly, use of naturally occurring grain and seeds enables provision of a predetermined range of water content. It is water content which is believed to provide the therapeutic benefit of the therapeutic pillow. A range of 5-25% water content by weight generally provides desired therapeutic results; the preferred range is 9-16% water content by weight. These ranges are considered critical to the efficacy of the therapeutic pillow. Those ordinarily skilled in the art will recognize that other and various materials providing these ranges of water content may be provided as a filler.

Figure 5:
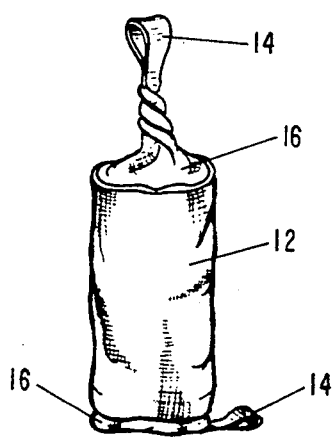
FIGS. 5 and 6 are perspective views of the pillow being prepared for application.
Figure 6:
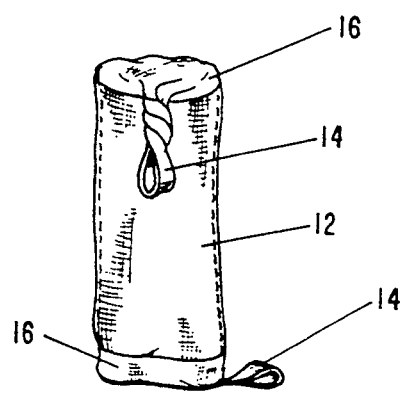

Ears 14 are sewn or otherwise attached to inner cover 16. Ears 14 are used for carrying, positioning, shaping and determining a given consistency for the therapeutic pillow, as shown in FIGS. 5 and 6.

Industrial Applicability

The invention is further illustrated by the following non-limiting examples.

EXAMPLE I

Assuming that it is desired to cool the affected body part, the therapeutic pillow is placed in a freezer at least 30 minutes prior to use. The therapeutic pillow may first be sealed in a plastic bag to prevent odor from attaching to the pillow. When applying the pillow, the desired consistency and firmness are first determined. The pillow is held up by one ear, allowed the filler contents to settle to the extent providing the desired firmness. The ear and attached inner cover are then twisted and tucked into the outer sleeve, as shown in FIGS. 5 and 6. The therapeutic pillow is then directly applied to the affected body part. For example, to relieve a stress-related headache, the cooled therapeutic pillow is wrapped about the neck while the subject is in a supine or sitting position.

EXAMPLE II

If it is desired to heat an affected body part, the therapeutic pillow may be warmed, for example, in a microwave oven. Depending upon its size, the pillow is heated no longer than 5 minutes and may be reheated hourly. Overheating is to be avoided. Again, as with cooling, and as depicted in FIGS. 5 and 6, the desired firmness is determined and the pillow is applied to the affected body part.

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above, and of the corresponding application(s), are hereby incorporated by reference.

What is claimed is:

1. A therapeutic pillow comprising a removable outer sleeve:

a baglike covering within said removable outer sleeve, wherein said baglike covering further comprises ears for grasping said therapeutic pillow;

said baglike covering containing a filling comprising natural granular material; and said natural granular material comprising a water content having a range of 5% to 25% by weight.

2. The invention of claim 1 wherein said outer sleeve is washable.

3. The invention of claim 2 wherein said washable outer sleeve comprises terry cloth fabric.

4. The invention of claim 1 wherein said baglike covering comprises cotton fabric.

5. The invention of claim 1 wherein said filling comprising natural granular material comprises processed barley.

6. The invention of claim 1 wherein said filling comprising natural granular material comprises seeds.

7. The invention of claim 1 wherein said water content comprises a preferred range of from 9% to 16% by weight.

8. A method of treating pain in an affected body part comprising the steps of:
   a) providing a baglike covering comprising ears for grasping;
   b) filling the baglike covering with natural granular material having a water content within the range of 5% to 25% by weight;
   c) loosely surrounding the baglike covering with a removable outer sleeve;
   d) heating or cooling the filled baglike covering and removable outer sleeve; and
   e) applying the heated or cooled filled baglike covering and removable outer sleeve to the affected body part.

9. The method of claim 8 wherein the step of filling the baglike covering with natural granular material comprises the step of filling the baglike covering with barley.

10. The method of claim 8 wherein the step of filling the baglike covering with natural granular material comprises the step of filling the baglike covering with seeds.

11. The method of claim 8 wherein the step of filling the baglike covering with natural granular material having a water content within the range of 5% to 25% by weight comprises the step of filling the baglike covering with natural granular material having a water content within the range of 9% to 16% by weight.

* * * * *